United States Patent
Canning et al.

(10) Patent No.: US 12,286,462 B2
(45) Date of Patent: *Apr. 29, 2025

(54) PORCINE G-CSF VARIANTS AND THEIR USES

(71) Applicants: Elanco US Inc., Greenfield, IN (US); Ambrx, Inc., La Jolla, CA (US)

(72) Inventors: Peter Connor Canning, Noblesville, IN (US); Nickolas Knudsen, Escondido, CA (US); Md Harunur Rashid, San Diego, CA (US)

(73) Assignees: Elanco US Inc., Greenfield, IN (US); Ambrx, Inc., La Jolla, CA (US)

(*) Notice: Subject to any disclaimer, the term of this patent is extended or adjusted under 35 U.S.C. 154(b) by 152 days.

This patent is subject to a terminal disclaimer.

(21) Appl. No.: 18/102,933

(22) Filed: Jan. 30, 2023

(65) Prior Publication Data

US 2023/0340051 A1    Oct. 26, 2023

Related U.S. Application Data

(63) Continuation of application No. 16/754,357, filed as application No. PCT/US2018/055203 on Oct. 10, 2018, now Pat. No. 11,578,111.

(60) Provisional application No. 62/570,877, filed on Oct. 11, 2017.

(51) Int. Cl.
| | |
|---|---|
| C07K 14/535 | (2006.01) |
| A61K 38/19 | (2006.01) |
| A61K 47/60 | (2017.01) |
| A61P 31/04 | (2006.01) |
| A61P 37/04 | (2006.01) |

(52) U.S. Cl.
CPC .......... *C07K 14/535* (2013.01); *A61K 38/193* (2013.01); *A61K 47/60* (2017.08); *A61P 31/04* (2018.01); *A61P 37/04* (2018.01)

(58) Field of Classification Search
None
See application file for complete search history.

(56) References Cited

U.S. PATENT DOCUMENTS

| | | | |
|---|---|---|---|
| 7,884,069 B2 | 2/2011 | Schaebitz et al. | |
| 2007/0141053 A1 | 6/2007 | Breimer et al. | |
| 2010/0035812 A1* | 2/2010 | Hays Putnam | A61P 31/00 435/325 |
| 2012/0082641 A1* | 4/2012 | Klotz | A61K 38/193 424/85.1 |
| 2015/0087602 A1* | 3/2015 | von Maltzahn | C07K 14/47 530/375 |
| 2021/0054039 A1 | 2/2021 | Canning et al. | |

FOREIGN PATENT DOCUMENTS

| | | |
|---|---|---|
| AU | 2013202836 A1 | 5/2013 |
| EA | 019968 B1 | 7/2014 |
| WO | 2000/044785 A1 | 8/2000 |
| WO | 2005/025593 A2 | 3/2005 |
| WO | 2005/074650 A2 | 8/2005 |
| WO | 2010/011735 A2 | 1/2010 |

OTHER PUBLICATIONS

Kulmburg et al. Cloningandsequenceanalysisoftheimmediatepromo terregionandcDNAofporcinegranulocytecolony-stimulatingfactor. Gene.Sep. 15, 1997,vol. 197,Nos. 1-2;pp. 361-365.*
Loving et al. Porcinegranulocyte-colonystimulatingfactor(G-CSF)deliveredviareplication defectiveadenovirusinducesasustained increaseincirculatingperipheralbloodneutrophils.Biologicals.Nov. 2013,vol. 41,No. 6;pp. 368-376.*
Deutscher; Methods in Enzymology, 182: 83-89 (1990).
Scopes; Protein Purification: Principles and Practice, 3rd Edition, Springer NY (1994).
Remington; The Science and Practice of Pharmacy, 19th ed., Gennara, ed. Mack Publishing co., Easton, PA (1995).
Kulmburg, P et al; Cloning and sequence analysis of the immediate promoter region and cDNA of porcine granulocyte colony-stimulating factor. Gene. Sep. 15, 1997, vol. 197, Nos. 1-2; pp. 361-365.
Loving, CL et al; Porcine granulocyte-colony stimulating factor (G-CSF) delivered via replication-defective adenovirus induces a sustained increase in circulating peripheral blood neutrophils. Biologicals. Nov. 2013, vol. 41, No. 6; pp. 368-376; p. 2.
GenBank Accession No. U68481.1.
Geneseq database, "Human Granulocyte Colony-Stimulating Factor (G-CSF) Mutant, H43X," XP002803220, retrieved from EBI accession No. GS_PROT:AAE30722, Feb. 24, 2003.
Geneseq database, "G-CSF mutant H44X," XP002803219, retrieved from EBI accession No. GS_PROT:AAR14737, Mar. 10, 2003.
Robbins, R. C., G. Almond, and E. Byers. "Swine Diseases and Disorders." Encyclopedia of Agriculture and Food Systems (2014): 261.
Witkowski, Andrzej, et al. "Conversion of a β-ketoacyl synthase to a malonyl decarboxylase by replacement of the active-site cysteine with glutamine." Biochemistry 38.36 (1999): 11643-11650. (Abstract).
Lockard, Joan S., et al. "Efficacy and toxicity of the solvent polyethylene glycol 400 in monkey model." Epilepsia 20.1 (1979): 77-84. (Abstract).
Aristizábal, Beatriz, and Ángel González. "Innate immune system." Autoimmunity: From Bench to Bedside [Internet]. El Rosario University Press, 2013. (Chapter 2).
Yen, Shui-Chen, MMA syndrome, Jun. 14, 2014, available at http://www.as3.nchu.edu.tw/sow-expert/aMMA%E7%B6%9C%E5% 90%88%E7%97%85%E5%BE%B5.aspx.

* cited by examiner

*Primary Examiner* — Maury A Audet
(74) *Attorney, Agent, or Firm* — Barnes & Thornburg LLP

(57) ABSTRACT

The present invention relates to variants of porcine granulocyte colony stimulating factor (pG-CSF). The pG-CSF variants are useful in treating preventing or reducing the incidence of bacterial infections in swine. Methods of treating swine are disclosed.

20 Claims, No Drawings
Specification includes a Sequence Listing.

PORCINE G-CSF VARIANTS AND THEIR USES

This application is a continuation of U.S. patent application Ser. No. 16/754,357, filed on Apr. 7, 2020, which is a national stage filing of PCT/US18/055203, filed Oct. 10, 2018, which claims the benefit of priority to U.S. Provisional patent application Ser. No. 62/570,877, filed Oct. 11, 2017, each of which is incorporated herein by reference in its entirety.

Incorporated by reference in its entirety is a computer-readable nucleotide/amino acid sequence listing submitted concurrently herewith and identified as follows: 27 kilobytes XML file named "78045-375714_ST26_020623," created on Feb. 6, 2023.

The present invention relates to variant porcine granulocyte colony stimulating factor (pG-CSF) polypeptides containing a synthetic amino acid. The synthetic amino acid is modified by attachment of a poly(ethylene glycol) (PEG) molecule. The PEGylated pG-CSF variant is used to treat bacterial infections in a porcine. When the porcine is a periparturient sow, the bacterial infection may be mastitis, metritis, and agalactia (MMA) syndrome. Reducing bacterial infections in pregnant sows improves piglet survival.

The economic impact of infectious diseases in food animal production is well documented. Infectious diseases reduce profits, increase production costs, and endanger food products, as well as affect the performance, health, and welfare of the animal. Diseases can cause morbidity and mortality of newborn, young (e.g., replacement stock) or adult animals, resulting in devastating effects on food animal production.

In porcines, one such disease may be mastitis, metritis, and agalactia (MMA) syndrome. Mastitis is a bacterial infection of the udder. Only one or two glands may be affected, or the infection could spread to multiple glands. Metritis is a bacterial infection of the urogenital tract, sometimes presented as vulval discharges. Agalactica is a reduction in, or the total loss of, milk production by a sow. MMA syndrome can be highly variable and may not present all the above symptoms. Thus, MMA syndrome can be difficult to detect and diagnose, and it may not be detected until a nursing piglet shows signs of hunger, weight loss, or even death.

Because MMA syndrome is difficult to detect, a prophylactic treatment is preferable. Use of antibiotics, particularly shared class antibiotics, is discouraged in food-producing animals, so a non-antibiotic therapy is preferable in the treatment of porcines. A cytokine such as pG-CSF could increase neutrophil numbers in an animal, thus priming the innate immune system to respond quickly to a bacterial infection. Modifying a pG-CSF variant with PEG could prolong the pharmokinetics and stability of the cytokine, thus potentiating its effects.

A PEGylated bovine G-CSF can be used to treat mastitis in dairy cattle (WO2010/011735). PEGylated human G-CSF has also been described (WO2000/044785). A PEGylated wild type porcine G-CSF has been proposed for the treatment of respiratory infections, such as viral infections (WO2005/025593). As disclosed in various aspects herein, a PEGylated pG-CSF variant elevates porcine blood neutrophil numbers, reduces the incidence of MMA syndrome in periparturient sows, and/or improves piglet survival.

The present invention provides porcine granulocyte colony stimulating factor (pG-CSF) variants having a consensus sequence of: $X_1$PLSPASSLPQSFLLK$X_2$LEQVRKIQADGAEL-QERLCATHKLC$X_3$PQELVLLGHSLGLP QASLSS-CSSQALQLTGCLNQLHGGLVLYQGLLQALAGISPE-LAPALDILQLDVTDLAT NIWLQ$X_4$EDLR$X_4$APASLPTQGTVPTFTSAFQRRA-GGVLVVSQLQSFLELAYRVLRYL AEP (SEQ ID NO: 13). The variable $X_1$ can be the dipeptide methionine alanine as in SEQ ID NOs: 2 and 9, the dipeptide norleucine alanine as in SEQ ID NOs: 7 and 10, alanine as in SEQ ID NOs: 4 and 11, or absent as in SEQ ID NOs: 8 and 12. The variable $X_2$ can be cysteine as in SEQ ID NOs: 2, 4, 7, and 8, or $X_2$ can be serine as in SEQ ID NOs: 9, 10, 11, and 12. The variable $X_3$ can be a synthetic amino acid. The synthetic amino acid can be present at position 43 (position relative to the mature wild-type pG-CSF as given in SEQ ID NO: 3) as shown in SEQ ID NO: 13. The synthetic amino acid can be para-acetyl phenylalanine (pAF). The variable $X_4$ can be methionine as in SEQ ID NOs: 2, 4, 8, 9, 11, and 12, or $X_4$ can be norleucine as in SEQ ID NOs: 7 and 10. The pAF synthetic amino acid can be covalently attached to a poly (ethylene glycol) (PEG) molecule. The PEG can have a molecular weight of about 20 kD to about 50 kD, or a molecular weight of about 30 kD. Preferably, the PEG is a linear PEG molecule.

The present invention provides a porcine granulocyte colony stimulating factor (pG-CSF) variant having a sequence of: MAPLSPASSLPQSFLLKCLEQVRKIQAD-GAELQERLCATHKLC[pAF]PQELVLLGHSL GLPQASLSSCSSQALQLTGCLNQLHG-GLVLYQGLLQALAGISPELAPALDILQLDVTD LAT-NIWLQMEDLRMAPASLPTQGTVPTFTSAFQR-RAGGVLVVSQLQSFLELAYRVLR YLAEP (SEQ ID NO: 2), wherein a para-acetyl phenylalanine (pAF) synthetic amino acid present at position 43 is covalently attached to a 30 kD linear PEG molecule.

The present invention provides a pharmaceutical composition comprising any of the pG-CSF variants described herein, and at least one pharmaceutically acceptable carrier, diluent, or excipient.

The present invention provides a method for treating a bacterial infection in a porcine comprising administering a therapeutically effective amount of any of the pG-CSF variants described herein to the porcine in need thereof. The bacterial infection may be mastitis, metritis and agalactia (MMA) syndrome. The porcine in need of treatment may be a periparturient sow. The therapeutically effective amount of a pG-CSF variant may be about 10-100 µg/kg animal weight, or about 30-50 µg/kg animal weight, or about 40 µg/kg animal weight. Administration of any of the pG-CSF variants described herein may occur at least once 7 days or less prior to farrowing (i.e. on or after day 107 of gestation), or at farrowing. In some aspects, the method of treating a bacterial infection in a porcine may comprise a second administration of any of the pG-CSF variants described herein within 14 days or less after farrowing (i.e., within 1, 2, 3, 4, 5, 6, 7, 8, 9, 10, 11, 12, 13 or within 14 days after farrowing).

The present invention provides a method for stimulating innate immune response in a porcine comprising administering a therapeutically effective amount of any of the pG-CSF variants described herein to the porcine in need thereof. The porcine in need of stimulation may be a periparturient sow. In other aspects the porcine in need of stimulation may be a porcine with a compromised or weakened immune system. In further aspects the porcine in need of stimulation may be a porcine that has or is at risk of developing an infection including, for example a bacterial infection or a viral infection. In some aspects, the method can stimulate production of cytokines (e.g., interferons (IFNs), tumor necrosis factors (TNFs), colony stimulating factors (CSFs), and/or interleukins (ILs)), and/or activate or increase levels of immune cells such as dendritic cells (DCs), lymphocytes (e.g., B cells, T cells, and natural killer (NK) cells), and myelocytes (e.g., Mast cells, myeloblasts (e.g., basophils, eosinophils, neutrophils, monocytes, and macrophages)). In some embodiments of these aspects, the method can stimulate or enhance neutrophil antibacterial function by, for example, increasing neutrophil myeloperoxidase-hydrogen peroxide-halide mediated antibacterial function.

In methods that stimulate the innate immune response, the therapeutically effective amount of a pG-CSF variant may be about 10-100 μg/kg animal weight, or about 30-50 μg/kg animal weight, or about 40 μg/kg animal weight. Administration of any of the pG-CSF variants described herein may occur at least once 7 days or less prior to farrowing (i.e. on or after day 107 of gestation), or at farrowing. In some aspects, the method of treating a bacterial infection in a porcine may comprise a second administration of any of the pG-CSF variants described herein within 14 days or less after farrowing (i.e., within 1, 2, 3, 4, 5, 6, 7, 8, 9, 10, 11, 12, 13 or within 14 days after farrowing).

The present invention provides a method for reducing piglet mortality comprising administering a therapeutically effective amount of any of the pG-CSF variants described herein to a periparturient sow. The therapeutically effective amount of a pG-CSF variant may be about 10-100 μg/kg animal weight, or about 30-50 μg/kg animal weight, or about 40 μg/kg animal weight. The administration of any of the pG-CSF variants described herein may occur at least once 7 days or less prior to farrowing (i.e. on or after day 107 of gestation), or at farrowing. In some aspects, the method of reducing piglet mortality may comprise a second administration to the periparturient sow of any of the pG-CSF variants described herein within 14 days or less after farrowing (i.e., within 1, 2, 3, 4, 5, 6, 7, 8, 9, 10, 11, 12, 13 or within 14 days after farrowing).

The present invention provides for use of any of the pG-CSF variants described herein in the manufacture of a medicament for a bacterial infection in a porcine. The bacterial infection may be MMA syndrome. The porcine may be a periparturient sow. The present invention provides for use of any of the pG-CSF variants described herein in the manufacture of a medicament for reducing piglet mortality.

The present invention provides any of the pG-CSF variants described herein for use in therapy. The therapy may be the treatment of a syndrome of bacterial infection in a porcine. The bacterial infection may be MMA syndrome. The porcine may be a periparturient sow.

The therapy may be the reduction of piglet mortality. The pG-CSF variant may be administered to a periparturient sow at about 10-100 μg/kg animal weight, or about 30-50 μg/kg animal weight, or about 40 μg/kg animal weight. The pG-CSF variant may be administered at least once 7 days or less prior to farrowing (i.e. on or after day 107 of gestation), or at farrowing. A second administration may be given to the periparturient sow 14 days or less after farrowing.

A "bacterial infection" is the growth of one or more bacterial species on or within the skin, mucus membranes, glands, eyes, ears, urogenital tract, digestive tract, lungs, blood or organs of an animal. The bacteria may be a species classified within the genera of *Achromobacter, Actinobacillus, Actinomyces, Bacillus, Bordatella, Brucella, Clostridium, Corynebacterium, Erysipelothrix, Escherichia, Haemophilus, Klebsiella, Leptospira, Listeria, Mycoplasmna, Pasteurella, Proteus, Pseudomonas, Salmonella, Sphaerophorus, Staphylococcus, Streptococcus,* or *Vibrio.*

The term "porcine" as used herein, refers to a pig, especially the domestic pig (*Sus scrofa domesticus* or *Sus domesticus*) and can include miniature pigs as well as those breeds raised for meat production. By "pig", "swine" or "porcine" is meant to include all pig breeds.

The periparturient sow is defined as the pregnant female porcine within the last weeks of gestation through the first few weeks post-farrowing. Farrowing, or giving birth, typically occurs at about 114 days of gestation. A periparturient sow could be a pregnant female porcine from about 100 days of gestation to about 14 days post-farrowing. A piglet is a porcine from birth to weaning at about 3 weeks of age.

A "synthetic amino acid" refers to an amino acid that is not one of the 20 common amino acids or pyrrolysine or selenocysteine. Examples of such synthetic amino acids include, but are not limited to, para-acetyl phenylalanine (pAF), acetylglucosaminyl-L-serine, and N-acetylglucosaminyl-L-threonine. Some synthetic amino acids and their incorporation into polypeptides and subsequent modification are described in WO2010/011735 and in WO2005/074650.

As used herein, the terms "treating", "to treat", or "treatment", include restraining, slowing, stopping, reducing, ameliorating, or reversing the progression or severity of a symptom, disorder, condition, or disease. In some aspects the disclosure provides methods that are specific to prophylactic treatment of a symptom, disorder, condition, or disease that is not observed or detected in an animal which may be at risk of developing one or more such symptom, disorder, condition, or disease. In some aspects, a treatment will be applied therapeutically.

The term "effective amount" as used refers to that amount of the pG-CSF variant being administered which will have the desired effect, such as preventing, treating, or reducing a bacterial infection in a porcine. When the porcine is a periparturient sow, treating bacterial infections in the sow can improve survival of piglets. The effective amount may vary with factors such as the weight of the sow.

By "administering" is meant the injection of a therapeutically effective amount of the compounds and compositions containing said compounds disclosed. For example without limitation, administration can be intramuscular (i.m) or subcutaneous (s.c.).

The term "about" will be understood by persons of ordinary skill in the art and will vary to some extent depending on the context in which it is used. As used herein, "about" is meant to encompass variations of ±10%, ±5%, or ±1% (i.e., ±10%, ±9%, ±8%, ±7%, ±6%, ±5%, ±4%, 3%, ±2%, or ±1%).

The pG-CSF variants of the present invention may readily be produced in a variety of cells including mammalian cells, bacterial cells such as *E. coli, Bacillus subtilis,* or *Pseudomonas fluorescence,* and/or in fungal or yeast cells. The host cells can be cultured using techniques well known in the art. The vectors containing the polynucleotide sequences of interest (e.g., the variants of pG-CSF and expression control sequences) can be transferred into the host cell by well-known methods, which vary depending on the type of cellular host. For example, the calcium chloride transformation method is commonly utilized for prokaryotic cells, whereas calcium phosphate treatment or electroporation may be used for other eukaryotic host cells. Various methods of protein purification may be employed and such methods are known in the art and described, for example, in Deutscher, *Methods in Enzymology* 182: 83-89 (1990) and Scopes, *Protein Purification: Principles and Practice,* 3rd Edition, Springer, NY (1994).

The PEGylated pG-CSF variants can be formulated according to known methods to prepare pharmaceutically useful compositions. In some aspects a formulation is a stable lyophilized product that is reconstituted with an appropriate diluent or an aqueous solution of high purity with optional pharmaceutically acceptable carriers, preservatives, excipients or stabilizers (see Remington, *The Science and Practice of Pharmacy*, 19th ed., Gennaro, ed., Mack Publishing Co., Easton, PA 1995).

The PEGylated pG-CSF variant may be formulated with a pharmaceutically acceptable buffer, and the pH adjusted to provide acceptable stability, and a pH acceptable for administration. In some non-limiting examples, a pH acceptable for administration may be in a range from about 5 to about 8 (i.e., about 5, about 6, about 7, or about 8). Moreover, the PEGylated pG-CSF compositions of the present invention may be placed into a container such as a vial, a cartridge, a pen delivery device, a syringe, intravenous administration tubing or an intravenous administration bag.

The following experimental examples are illustrative of pG-CSF variants, and their use in treating bacterial infections in swine, such as MMA syndrome in a periparturient sow. Reducing the incidence of bacterial infections in the sow also reduces piglet mortality. It will be appreciated that other embodiments and uses will be apparent to those skilled in the art and that the invention is not limited to these specific illustrative examples or preferred embodiments.

EXAMPLE 1

Different variants of the porcine granulocyte colony stimulating factor (pG-CSF) cDNA (GenBank Accession number U68481.1) are generated by introducing a TAG stop codon in the selected positions by site-directed PCR mutagenesis. Also, the portion of the cDNA encoding the signal sequence is replaced by a single methionine codon (i.e. ATG). For example, a cDNA encoding wild type mature pG-CSF with the altered signal sequence could be:

```
  1 atggccctc tcagccctgc cagctccctg ccccagagct tcctgctcaa gtgcttagag 61 caagtgagga aaatccaggc tgatggcgcc gagctgcagg agaggctgtg tgccacccac 121 aagctgtgcc accccagga gctggtgctg ctcgggcact ctctgggcct ccccaggct 181 tccctgagca gctgctccag ccaggccctg cagctgactg gctgcctgaa ccaactgcat 241 ggcggcctcg tcctctacca gggcctcctg caggccctgg cgggcatctc cccagagctg 301 gccccgccc tggacatact gcagctggat gtcaccgact tagccaccaa catctggctg 361 cagatggaag acctgaggat ggccccggcc tcgcttccca cccagggcac cgtgccgacc 421 ttcacctcgg ccttccagcg ccgggcagga ggggtcctgg ttgtctccca gctgcagagc
```

```
481 ttcctggagc tggcgtaccg tgtcctgcgc tacctcgccg agccctga
```

(SEQ ID NO: 5). This variant would encode a polypeptide of:

```
  1   MAPLSPASSL PQSFLLKCLE QVRKIQADGA

ELQERLCATH KLCHPQELVL LGHSLGLPQA

61   SLSSCSSQAL QLTGCLNQLH GGLVLYQGLL

QALAGISPEL APALDILQLD VTDLATNIWL

121   QMEDLRMAPA SLPTQGTVPT FTSAFQRRAG

GVLVVSQLQS FLELAYRVLR
```

(SEQ ID NO: 1). If the TAG stop codon is desired to replace the H43 residue, the cDNA sequence could be:

```
  1 atggccctc tcagccctgc cagctccctg ccccagagct tcctgctcaa gtgcttagag 61 caagtgagga aaatccaggc tgatggcgcc gagctgcagg agaggctgtg tgccacccac 121 aagctgtgct ilgccccagga gctggtgctg ctcgggcact ctctgggcct ccccaggct 181 tccctgagca gctgctccag ccaggccctg cagctgactg gctgcctgaa ccaactgcat 241 ggcggcctcg tcctctacca gggcctcctg caggccctgg cgggcatctc cccagagctg 301 gccccgccc tggacatact gcagctggat gtcaccgact tagccaccaa catctggctg 361 cagatggaag acctgaggat ggccccggcc tcgcttccca cccagggcac cgtgccgacc 421 ttcacctcgg ccttccagcg ccgggcagga ggggtcctgg ttgtctccca gctgcagagc 481 ttcctggagc tggcgtaccg tgtcctgcgc tacctcgccg agccctga
```

(SEQ ID NO: 6). The resulting polypeptide would be:

```
  1 MAPLSPASSL PQSFLLKCLE QVRKIQADGA

ELQERLCATH KLCxPQELVL LGHSLGLPQA

61 SLSSCSSQAL QLTGCLNQLH GGLVLYQGLL

QALAGISPEL APALDILQLD VTDLATNIWL

121 QMEDLRMAPA SLPTQGTVPT FTSAFQRRAG

GVLVVSQLQS FLELAYRVLR YLAEP
```

(SEQ ID NO: 2), where the "x" indicates the H43 residue replaced with a synthetic amino acid, as described below.

Plasmids encoding the variants are transformed into *E. coli* cells containing the expanded genetic code system components for incorporation of the synthetic amino acid para-acetyl phenylalanine (pAF). Transformed cells are grown in media supplemented with pAF and induced to express pG-CSF with pAF incorporated into the sites indicated. The expression system has been described, for example, in WO 2010/011735 (incorporated herein by reference), and is generally known in the art.

Expression of the transfected cDNA variants is induced with arabinose, the cells are harvested, and the target pG-CSF pAF site variants are isolated and purified by reverse phase high-pressure liquid chromatography (RP-HPLC). An activated 30 kD linear aminooxy-PEG is site-specifically conjugated to the incorporated pAF. PEG-pG-CSF conjugates are purified from excess PEG and unconjugated pG-CSF variants by chromatography.

EXAMPLE 2

The in vitro biological activity of PEGylated pG-CSF (PEG-pG-CSF) variants is measured by the ability of the variants to induce proliferation of M-NSF-60 cells (ATCC CRL-1838). The concentration of the variants able to effect 50% of maximal proliferation ($EC_{50}$) is determined by comparison to a standard curve generated with wild type (WT) pG-CSF. Based on the results of expression as presented in Example 1 and the biological assays described here, PEG-pG-CSF variants are selected for further study.

The in vivo activity of the selected candidate PEG-pG-CSF variants is tested in a rodent model. Sprague Dawley rats (3/group) are treated with 0.25 mg/kg body weight with a PEG-pG-CSF variant. Blood samples are taken at O (pre-dosing), 1, 3, 6, 24, 48, 56, 72, 96, 144, 192, and 264 hours for pharmokinetic (PK) analysis, and samples are taken at 24, 48, 72, and 96 hours for a complete blood count (CBC analysis). The primary measurement in the CBC analysis is the number of neutrophils present. A H43 variant stimulates a higher level of neutrophil development than other variants tested. All variants have similar PK profiles.

EXAMPLE 3

The PEG-pG-CSF H43pAF is prepared as follows. As in Example 1, expression of the transfected cDNA variants is induced with arabinose, the cells are harvested, and the pG-CSF H43pAF site variant is isolated, denatured and refolded, and purified by cation exchange liquid chromatography (CEX), using CAPTO Adhere Impres (GE Healthcare Lifesciences). Briefly, the unpegylated pG-CSF H43pAF variant is loaded onto the column to a concentration of 1-5 mg/mL resin. The column is washed with five column volumes (CV) 30 mM sodium acetate at pH 4.5. Elution of the pG-CSF H43pAF variant is with a linear gradient of elution buffer (30 mM sodium acetate, 0.5 M NaCl, Ph 4.5), by washing with 0-100% elution buffer over 20 CV.

Based on mass spectroscopy (MS) analysis of pG-CSF H43pAF, the isolated peptides include a main peak represented by SEQ ID NO: 2 and several different contaminants. The contaminants include loss of the N-terminal methione (SEQ ID NO: 4), loss of both the N-terminal methionine and alanine (SEQ ID NO: 8), and substitution of norleucine for the N-terminal methionine (SEQ ID NO: 7). Norleucine is known to be misincorporated instead of the amino acid methionine in high density fermentation with E. coli. Norleucine incorporation is reduced by using one or more of the following steps: feeding the fermentation solutions with methionine; fermenting with complex media instead of defined media (the complex media has one or more non-defined components in it including but not limited to glycerol, salts, amino acids, vitamins, yeast extracts, plant and animal hydrolysates, peptones, and tryptones); and/or lowering the temperature of the fermentation reaction mixture post induction.

The pG-CSF H43pAF variant is taken from the cation exchange chromatography pool after using Capto SP Impres chromatography and buffer exchanged into 30 mM sodium acetate, 4% sucrose, pH 4.0 using a 10 kDa MWCO tangential flow filtration cassette. The pG-CSF H43pAF variant is then concentrated to about 8.0 mg/mL using an Amicon Ultra centrifugal filter according to manufacturer's instructions. Once concentrated, 30K linear PEG (PEG can be purchased commercially from NOF America Corporation or EMD Merck, for example) is added in a 6:1 molar ratio of PEG to pG-CSF H43pAF variant. The PEG/pG-CSF variant mixture is then incubated at about 28° C. for at least 21 hours. This method results in >98% of the pG-CSF variant being conjugated with PEG. The pegylated variant can then be purified by CEX as above. When tested in the M-NSF-60 cell bioassay (Example 2), the PEG-pG-CSF H43pAF variant has an $EC_{50}$ of at least 0.40 ng/mL, demonstrating good binding and potency characteristics.

Samples are frozen and thawed over five cycles by freezing at 0° C. in 1.5 mL tubes and thawing in a room temperature water bath. No significant impact is observed for the high molecular weight (HMW) protein profile over five cycles of freeze-thawing, demonstrating the stability of the variant in solution.

Two additional pG-CSF H43pAF variants are generated to attempt to improve refolding efficiency and thermostability of the variant at 50° C. Cysteine 17 is changed to either alanine (C17A) or to serine (C17S, SEQ ID NOs: 9-12). These mutations do not improve refolding yield, but C17A has decreased thermostability. PEG-pG-CSF H43pAF/C17S does have a slightly improved $EC_{50}$ of 0.26 ng/mL.

EXAMPLE 4

The PEG-pG-CSF H43pAF variant is administered to sows to characterize changes in blood neutrophils. Six sows of 1.5-5 years of age and an average body weight of 269.7 kg are given 40 µg/kg of the PEG-pG-CSF H43pAF variant by intramuscular injection on the side of the neck. The PEG-pG-CSF H43pAF variant is suspended in 30 mM sodium citrate, 250 mM arginine, pH 6.0 at a concentration of 8.2 mg/mL. Animals do not receive any concomitant medication following initiation of treatment. No adverse events are observed.

Blood is taken on day 0 prior to dosing and on days 2, 7, 10, 14, 17 and 21 post-dosing. Neutrophil counts are determined for each sow and a mean for the treatment is determined for each day. Treatment with a single dose of the PEG-pG-CSF H43pAF variant results in measurable increases in blood neutrophil counts over a three-week period (Table 1). Additional doses would be expected to stimulate maintenance of the higher neutrophil levels.

TABLE 1

Effect of PEG-pG-CSF H43pAF variant on mean daily blood neutrophil counts.

| | Day | | | | | | |
|---|---|---|---|---|---|---|---|
| | 0 | 2 | 7 | 10 | 14 | 17 | 21 |
| Neutrophils (1000/µL) | 4.65 | 43.68 | 25.08 | 30.1 | 18.53 | 15.14 | 9.83 |

EXAMPLE 5

The PEG-pG-CSF H43pAF variant is administered to periparturient sows to characterize the effect on mastitis, metritis, and agalactia (MMA) syndrome and on piglet survival.

Sows at 95-100 days of gestation are placed into farrowing crates and hygienic husbandry practices are followed until day 107 of gestation for each sow. On day 107, blood is collected and then the sows (25 per group) are treated either with 40 pig/kg of the PEG-pG-CSF H43pAF variant as in Example 4 or with a sodium chloride solution as a negative control. The sows are then placed in unhygienic conditions to stimulate development of MMA. The unhygienic conditions include placing a mat on the grated floor of the farrowing crate to allow bedding and waste material to accumulate. Also, a mixture of water, feces, and pine sawdust (2:1:1) is used to contaminate the crates. No oxytocic or corticosteroid drugs are given to the sows. Clinical observations and rectal temperatures are collected on each sow once daily in the morning beginning on day 107 of gestation and continuing until a diagnosis of MMA at which time the sow has all samples collected and is then removed from the study, given treatment, and has hygienic crate conditions returned. Samples collected include blood, rectal temperature, and swabs of infected glands.

Farrowing typically occurs on day 114 of gestation. Piglets are weighed and tagged within 12 hours of birth. Clinical observations of the piglets are made twice daily, and weights are also measured on days 3, 7, and 21 after birth.

Using the per protocol definition of disease, little difference was observed between the two groups. However, when vulvar discharge was removed from the definition of disease, the incidence of disease was reduced by more than 50% in the PEG-pG-CSF treated group. The treated group also had a greater number of piglets weaned compared to control group (Table 2).

TABLE 2

Effect of PEG-pG-CSF on MMA incidence and piglet survival.

| Variable | Control | PEG-pG-CSF | P value |
|---|---|---|---|
| Sows (number/group) | | | |
| MMA | 36% (9/25) | 32% (8/35) | 1.0000 |
| MMA excluding vulvar discharge | 28% (7/25) | 12% (3/25) | 0.2890 |
| Piglets (Std. Error of Mean) | | | |
| Number born/litter | 13.3 (0.78) | 13.1 (0.72) | 0.8567 |
| Number weaned/litter | 8.3 (0.61) | 9.4 (0.61) | 0.2056 |
| Percent survival | 65.3 (4.5) | 72.4 (4.3) | 0.2590 |
| Range survival/litter | 0-100% | 38-100% | n/a |
| Weaning weight | 5.9 (0.21) | 5.7 (0.19) | 0.5944 |

What is claimed is:

1. A porcine granulocyte colony stimulating factor (pG-CSF) variant comprising the amino acid sequence of:

(SEQ ID NO: 13)
X$_1$PLSPASSLPQSFLLKX$_2$LEQVRKIQADGAELQERLC

ATHKLC(pAF)PQELVLLGHSLGLPQASLSSCSSQAL

QLTGCLNQLHGGLVLYQGLLQALAGISPELAPALDIL

QLDVTDLATNIWLQX$_3$EDLRX$_3$APASLPTQGTVPTFTS

AFQRRAGGVLVVSQLQSFLELAYRVLRYLAEP;

wherein X$_1$ is selected from the group of methionine alanine, norleucine alanine, alanine only, and no amino acids;
wherein X$_2$ is cysteine or serine;
wherein X$_3$ is methionine or norleucine; and
wherein a para-acetyl phenylalanine (pAF) synthetic amino acid present at position 43 is covalently attached to a poly(ethylene glycol) (PEG).

2. The pG-CSF variant of claim 1, wherein the PEG has a molecular weight of about 20 kD to about 50 kD.

3. The pG-CSF variant of claim 1, wherein the PEG has a molecular weight of about 30 kD.

4. The pG-CSF variant of claim 1, wherein the PEG is linear.

5. The pG-CSF variant of claim 1,
wherein the para-acetyl phenylalanine (pAF) synthetic amino acid present at position 43 is covalently attached to a 30 kD linear PEG.

6. A pharmaceutical composition comprising the pG-CSF variant of claim 1, and at least one pharmaceutically acceptable carrier, diluent, or excipient.

7. A method for treating a MMA syndrome in a porcine comprising administering a therapeutically effective amount of the pG-CSF variant of claim 1 to the porcine in need thereof.

8. The method of claim 7, wherein the MMA syndrome comprises symptoms of is mastitis, metritis and agalactia.

9. The method of claim 7, wherein the porcine is a periparturient sow.

10. The method of claim 7, wherein the therapeutically effective amount of pG-CSF is about 10-100 µg/kg animal weight.

11. The method of claim 7, wherein the therapeutically effective amount of pG-CSF is about 30-50 µg/kg animal weight.

12. The method of claim 7, wherein the administering occurs at least once within 7 days prior to farrowing.

13. The method of claim 7, wherein the administering occurs at farrowing.

14. The method of claim 7, further comprising a second administration no later than 14 days after farrowing.

15. A method for increasing blood neutrophils in a porcine comprising administering a therapeutically effective amount of the pG-CSF variant of claim 1 to the porcine.

16. The method of claim 15, wherein the therapeutically effective amount of pG-CSF is about 10-100 µg/kg animal weight.

17. The method of claim 15, wherein the administering occurs at least once within 7 days prior to farrowing.

18. The method of claim 15, wherein the administering occurs at farrowing.

19. The method of claim 17, further comprising a second administration no later than 14 days after farrowing.

20. A method for stimulating innate immune response by increasing blood neutrophils in a porcine comprising administering a therapeutically effective amount of the pG-CSF variant of claim 1 to the porcine in need thereof.

* * * * *

SEQUENCE LISTING

```
Sequence total quantity: 13
SEQ ID NO: 1            moltype = AA  length = 175
FEATURE                 Location/Qualifiers
REGION                  1..175
                        note = porcine granulocyte colony stimulating factor variant
source                  1..175
                        mol_type = protein
                        organism = synthetic construct
SEQUENCE: 1
MAPLSPASSL PQSFLLKCLE QVRKIQADGA ELQERLCATH KLCHPQELVL LGHSLGLPQA   60
SLSSCSSQAL QLTGCLNQLH GGLVLYQGLL QALAGISPEL APALDILQLD VTDLATNIWL  120
QMEDLRMAPA SLPTQGTVPT FTSAFQRRAG GVLVVSQLQS FLELAYRVLR YLAEP       175

SEQ ID NO: 2            moltype = AA  length = 175
FEATURE                 Location/Qualifiers
REGION                  1..175
                        note = porcine granulocyte colony stimulating factor variant
SITE                    44
                        note = para-acetyl phenylalanine
source                  1..175
                        mol_type = protein
                        organism = synthetic construct
SEQUENCE: 2
MAPLSPASSL PQSFLLKCLE QVRKIQADGA ELQERLCATH KLCXPQELVL LGHSLGLPQA   60
SLSSCSSQAL QLTGCLNQLH GGLVLYQGLL QALAGISPEL APALDILQLD VTDLATNIWL  120
QMEDLRMAPA SLPTQGTVPT FTSAFQRRAG GVLVVSQLQS FLELAYRVLR YLAEP       175

SEQ ID NO: 3            moltype = AA  length = 174
FEATURE                 Location/Qualifiers
REGION                  1..174
                        note = mature wild-type porcine granulocyte colony
                        stimulating factor
source                  1..174
                        mol_type = protein
                        organism = Sus scrofa
SEQUENCE: 3
APLSPASSLP QSFLLKCLEQ VRKIQADGAE LQERLCATHK LCHPQELVLL GHSLGLPQAS   60
LSSCSSQALQ LTGCLNQLHG GLVLYQGLLQ ALAGISPELA PALDILQLDV TDLATNIWLQ  120
MEDLRMAPAS LPTQGTVPTF TSAFQRRAGG VLVVSQLQSF LELAYRVLRY LAEP        174

SEQ ID NO: 4            moltype = AA  length = 174
FEATURE                 Location/Qualifiers
REGION                  1..174
```

```
                         note = porcine granulocyte colony stimulating factor variant
SITE                     43
                         note = para-acetyl phenylalanine
source                   1..174
                         mol_type = protein
                         organism = synthetic construct
SEQUENCE: 4
APLSPASSLP QSFLLKCLEQ VRKIQADGAE LQERLCATHK LCXPQELVLL GHSLGLPQAS    60
LSSCSSQALQ LTGCLNQLHG GLVLYQGLLQ ALAGISPELA PALDILQLDV TDLATNIWLQ   120
MEDLRMAPAS LPTQGTVPTF TSAFQRRAGG VLVVSQLQSF LELAYRVLRY LAEP         174

SEQ ID NO: 5             moltype = DNA  length = 528
FEATURE                  Location/Qualifiers
misc_feature             1..528
                         note = cDNA encodes SEQ ID NO: 1&3
source                   1..528
                         mol_type = other DNA
                         organism = synthetic construct
SEQUENCE: 5
atggcccctc tcagccctgc cagctccctg cccagagct tcctgctcaa gtgcttagag     60
caagtgagga aatccaggc tgatggcgcc gagctgcagg agaggctgtg tgccacccac    120
aagctgtgcc accccagga gctggtgctg ctcgggcact ctctgggcct ccccaggct    180
tccctgagca gctgctccag ccaggccctg cagctgactg gctgcctgaa ccaactgcat   240
ggcggcctcg tcctctacca gggcctcctg caggccctgg cgggcatctc cccagagctg   300
gcccccgccc tggacatact gcagctggat gtcaccgact tagccaccaa catctggctg   360
cagatggaag acctgaggat ggccccggcc tcgcttccca cccagggcac cgtgccgacc   420
ttcacctcgg ccttccagcg ccgggcagga ggggtcctgg ttgtctccag gctgcagagc   480
ttcctggagc tggcgtaccg tgtcctgcgc tacctcgccg agccctga               528

SEQ ID NO: 6             moltype = DNA  length = 528
FEATURE                  Location/Qualifiers
misc_feature             1..528
                         note = cDNA encodes SEQ ID NO: 2&4
source                   1..528
                         mol_type = other DNA
                         organism = synthetic construct
SEQUENCE: 6
atggcccctc tcagccctgc cagctccctg cccagagct tcctgctcaa gtgcttagag     60
caagtgagga aatccaggc tgatggcgcc gagctgcagg agaggctgtg tgccacccac    120
aagctgtgct agccccagga gctggtgctg ctcgggcact ctctgggcct ccccaggct    180
tccctgagca gctgctccag ccaggccctg cagctgactg gctgcctgaa ccaactgcat   240
ggcggcctcg tcctctacca gggcctcctg caggccctgg cgggcatctc cccagagctg   300
gcccccgccc tggacatact gcagctggat gtcaccgact tagccaccaa catctggctg   360
cagatggaag acctgaggat ggccccggcc tcgcttccca cccagggcac cgtgccgacc   420
ttcacctcgg ccttccagcg ccgggcagga ggggtcctgg ttgtctccca gctgcagagc   480
ttcctggagc tggcgtaccg tgtcctgcgc tacctcgccg agccctga               528

SEQ ID NO: 7             moltype = AA  length = 175
FEATURE                  Location/Qualifiers
REGION                   1..175
                         note = porcine granulocyte colony stimulating factor variant
VARIANT                  1
                         note = norleucine or methionine
SITE                     44
                         note = para-acetyl phenylalanine
VARIANT                  122
                         note = norleucine or methionine
VARIANT                  127
                         note = norleucine or methionine
source                   1..175
                         mol_type = protein
                         organism = synthetic construct
SEQUENCE: 7
XAPLSPASSL PQSFLLKCLE QVRKIQADGA ELQERLCATH KLCXPQELVL LGHSLGLPQA    60
SLSSCSSQAL QLTGCLNQLH GGLVLYQGLL QALAGISPEL APALDILQLD VTDLATNIWL   120
QXEDLRXAPA SLPTQGTVPT FTSAFQRRAG GVLVVSQLQS FLELAYRVLR YLAEP        175

SEQ ID NO: 8             moltype = AA  length = 173
FEATURE                  Location/Qualifiers
REGION                   1..173
                         note = porcine granulocyte colony stimulating factor variant
SITE                     42
                         note = para-acetyl phenylalanine
source                   1..173
                         mol_type = protein
                         organism = synthetic construct
SEQUENCE: 8
PLSPASSLPQ SFLLKCLEQV RKIQADGAEL QERLCATHKL CXPQELVLLG HSLGLPQASL    60
SSCSSQALQL TGCLNQLHGG LVLYQGLLQA LAGISPELAP ALDILQLDVT DLATNIWLQM   120
```

```
EDLRMAPASL PTQGTVPTFT SAFQRRAGGV LVVSQLQSFL ELAYRVLRYL AEP        173

SEQ ID NO: 9              moltype = AA  length = 175
FEATURE                   Location/Qualifiers
REGION                    1..175
                          note = porcine granulocyte colony stimulating factor variant
SITE                      44
                          note = para-acetyl phenylalanine
source                    1..175
                          mol_type = protein
                          organism = synthetic construct
SEQUENCE: 9
MAPLSPASSL PQSFLLKSLE QVRKIQADGA ELQERLCATH KLCXPQELVL LGHSLGLPQA  60
SLSSCSSQAL QLTGCLNQLH GGLVLYQGLL QALAGISPEL APALDILQLD VTDLATNIWL 120
QMEDLRMAPA SLPTQGTVPT FTSAFQRRAG GVLVVSQLQS FLELAYRVLR YLAEP      175

SEQ ID NO: 10             moltype = AA  length = 175
FEATURE                   Location/Qualifiers
REGION                    1..175
                          note = porcine granulocyte colony stimulating factor variant
VARIANT                   1
                          note = norleucine or methionine
SITE                      44
                          note = para-acetyl phenylalanine
VARIANT                   122
                          note = norleucine or methionine
VARIANT                   127
                          note = norleucine or methionine
source                    1..175
                          mol_type = protein
                          organism = synthetic construct
SEQUENCE: 10
XAPLSPASSL PQSFLLKSLE QVRKIQADGA ELQERLCATH KLCXPQELVL LGHSLGLPQA  60
SLSSCSSQAL QLTGCLNQLH GGLVLYQGLL QALAGISPEL APALDILQLD VTDLATNIWL 120
QXEDLRXAPA SLPTQGTVPT FTSAFQRRAG GVLVVSQLQS FLELAYRVLR YLAEP      175

SEQ ID NO: 11             moltype = AA  length = 174
FEATURE                   Location/Qualifiers
REGION                    1..174
                          note = porcine granulocyte colony stimulating factor variant
SITE                      43
                          note = para-acetyl phenylalanine
source                    1..174
                          mol_type = protein
                          organism = synthetic construct
SEQUENCE: 11
APLSPASSLP QSFLLKCLEQ VRKIQADGAE LQERLCATHK LCXPQELVLL GHSLGLPQAS  60
LSSCSSQALQ LTGCLNQLHG GLVLYQGLLQ ALAGISPELA PALDILQLDV TDLATNIWLQ 120
MEDLRMAPAS LPTQGTVPTF TSAFQRRAGG VLVVSQLQSF LELAYRVLRY LAEP       174

SEQ ID NO: 12             moltype = AA  length = 173
FEATURE                   Location/Qualifiers
REGION                    1..173
                          note = porcine granulocyte colony stimulating factor variant
SITE                      42
                          note = para-acetyl phenylalanine
source                    1..173
                          mol_type = protein
                          organism = synthetic construct
SEQUENCE: 12
PLSPASSLPQ SFLLKSLEQV RKIQADGAEL QERLCATHKL CXPQELVLLG HSLGLPQASL  60
SSCSSQALQL TGCLNQLHGG LVLYQGLLQA LAGISPELAP ALDILQLDVT DLATNIWLQM 120
EDLRMAPASL PTQGTVPTFT SAFQRRAGGV LVVSQLQSFL ELAYRVLRYL AEP        173

SEQ ID NO: 13             moltype = AA  length = 174
FEATURE                   Location/Qualifiers
REGION                    1..174
                          note = porcine granulocyte colony stimulating factor variant
VARIANT                   1
                          note = any naturally occurring amino acid
VARIANT                   17
                          note = any naturally occurring amino acid
SITE                      43
                          note = para-acetyl phenylalanine
VARIANT                   121
                          note = any naturally occurring amino acid
VARIANT                   126
                          note = any naturally occurring amino acid
source                    1..174
```

```
                    mol_type = protein
                    organism = synthetic construct
SEQUENCE: 13
XPLSPASSLP QSFLLKXLEQ VRKIQADGAE LQERLCATHK LCXPQELVLL GHSLGLPQAS    60
LSSCSSQALQ LTGCLNQLHG GLVLYQGLLQ ALAGISPELA PALDILQLDV TDLATNIWLQ   120
XEDLRXAPAS LPTQGTVPTF TSAFQRRAGG VLVVSQLQSF LELAYRVLRY LAEP         174
```